United States Patent
Yao et al.

(10) Patent No.: US 11,621,420 B2
(45) Date of Patent: Apr. 4, 2023

(54) HIGH IONIC CONDUCTIVITY RECHARGEABLE SOLID STATE BATTERIES WITH AN ORGANIC ELECTRODE

(71) Applicant: University of Houston System, Houston, TX (US)

(72) Inventors: Yan Yao, Pearland, TX (US); Yanliang Liang, Houston, TX (US)

(73) Assignee: University of Houston System, Houston, TX (US)

(*) Notice: Subject to any disclaimer, the term of this patent is extended or adjusted under 35 U.S.C. 154(b) by 791 days.

(21) Appl. No.: 16/083,994

(22) PCT Filed: Mar. 13, 2017

(86) PCT No.: PCT/US2017/022025
§ 371 (c)(1),
(2) Date: Sep. 11, 2018

(87) PCT Pub. No.: WO2017/156518
PCT Pub. Date: Sep. 14, 2017

(65) Prior Publication Data
US 2020/0295369 A1    Sep. 17, 2020

Related U.S. Application Data

(60) Provisional application No. 62/307,079, filed on Mar. 11, 2016.

(51) Int. Cl.
*H01M 4/60* (2006.01)
*C07C 50/04* (2006.01)
(Continued)

(52) U.S. Cl.
CPC ............... *H01M 4/60* (2013.01); *C07C 50/04* (2013.01); *H01M 4/381* (2013.01); *H01M 4/382* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 5,512,391 | A | 4/1996 | Fleischer |
| 7,018,604 | B2 | 3/2006 | Poling et al. |

(Continued)

FOREIGN PATENT DOCUMENTS

| JP | S55161374 A | 12/1980 | |
|---|---|---|---|
| JP | H10289617 | 10/1998 | |
| JP | 2009093880 A | * 4/2009 | ............. Y02E 60/10 |

OTHER PUBLICATIONS

Ryoji Kanno and Masahiro Murayama, "Lithium Ionic Conductor Thio-LISICON: The Li2S—GeS2—P2S5 System", Journal of The Electrochemical Society, 148 (7) A742-A746. (Year: 2001).*

(Continued)

*Primary Examiner* — Matthew T Martin
*Assistant Examiner* — Jessie L. Walls
(74) *Attorney, Agent, or Firm* — Shackelford, Bowen, McKinely & Norton, LLP

(57) ABSTRACT

An improved rechargeable battery may utilize materials that are entirely solid-state. The battery may utilize at least one organic active material for an electrode. The battery may utilize a cathode that comprises quinone(s). An electrolyte of the battery may be an ion-conducting inorganic compound. An anode of the battery may comprise an alkali metal. Further, a carbonyl group of the quinone(s) of the cathode (Continued)

may be reduced into a phenolate and coordinated to an alkali metal ion during discharge and vice versa during charging.

7 Claims, 5 Drawing Sheets

(51) Int. Cl.
*H01M 4/38* (2006.01)
*H01M 4/40* (2006.01)
*H01M 10/0525* (2010.01)
*H01M 10/054* (2010.01)
*H01M 10/0562* (2010.01)
*H01M 10/058* (2010.01)

(52) U.S. Cl.
CPC ............ *H01M 4/40* (2013.01); *H01M 4/405* (2013.01); *H01M 4/606* (2013.01); *H01M 10/054* (2013.01); *H01M 10/058* (2013.01); *H01M 10/0525* (2013.01); *H01M 10/0562* (2013.01); *H01M 2300/0068* (2013.01)

(56) References Cited

U.S. PATENT DOCUMENTS

| | | |
|---|---|---|
| 7,101,527 B1 | 9/2006 | Poling et al. |
| 10,033,039 B2 | 7/2018 | Yao et al. |
| 2011/0039162 A1 | 2/2011 | Maeda |
| 2012/0196182 A1* | 8/2012 | Yao .................. H01M 10/0525 429/213 |
| 2012/0301778 A1 | 11/2012 | Trevey et al. |
| 2014/0308581 A1 | 10/2014 | Yao et al. |
| 2014/0377664 A1 | 12/2014 | Yersak et al. |
| 2015/0044556 A1* | 2/2015 | Wang ...................... H01M 4/13 429/231.1 |
| 2018/0301763 A1 | 10/2018 | Yao et al. |
| 2020/0052350 A1* | 2/2020 | Zhamu .................. H01M 4/625 |

OTHER PUBLICATIONS

Gottis et al., "Voltage Gain in Lithiated Enolate-Based Organic Cathode Materials by Isomeric Effect" ACS Appl. Mater. Interfaces 2014, 6, 10870-10876, <dx.doi.org/10.1021/am405470p > (Year: 2014).*

Xingchao Wang, Zhenfeng Shang, Aikai Yang, Qiu Zhang, Fangyi Cheng, Dianzeng Jia, Jun Chen; ("Combining Quinone Cathode and Ionic Liquid Electrolyte for Organic Sodium-Ion Batteries", CellPress, Chem 5, 364-375 Feb. 14, 2019, Elsevier Inc. https://doi.org/10.1016/j.chempr.2018.10.018 (Year: 2019).*

Zhu et al., "All-Solid-State Lithium Organic Battery with Composite Polymer Electrolyte and Pillar[5]quinone Cathode", J. Am. Chem. Soc., 2014, 136 (47), 16461-16464.

Supporting Information for Zhu et al., "All-Solid-State Lithium Organic Battery with Composite Polymer Electrolyte and Pillar[5]quinone Cathode", J. Am. Chem. Soc., 2014, 136 (47), pp. 16461-16464.

Hao et al., High-Energy All-Solid-State Organic-Lithium Batteries Based on Ceramic Electrolytes, ACS Energy Lett. 2021, 6, 201-207.

Lécuyer et al., A rechargeable lithium/quinone battery using a commercial polymer electrolyte, Electrochemistry Communications 55 (2015) 22-25.

* cited by examiner a
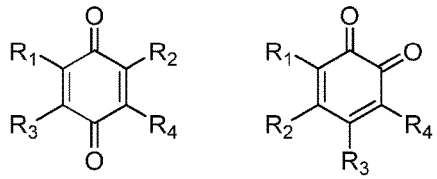
b
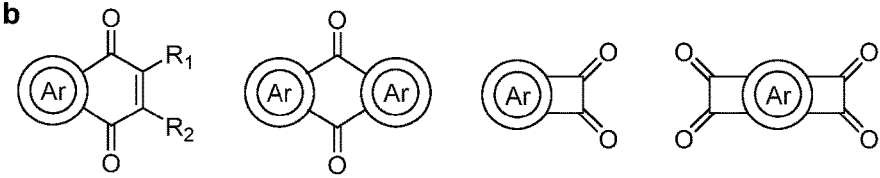
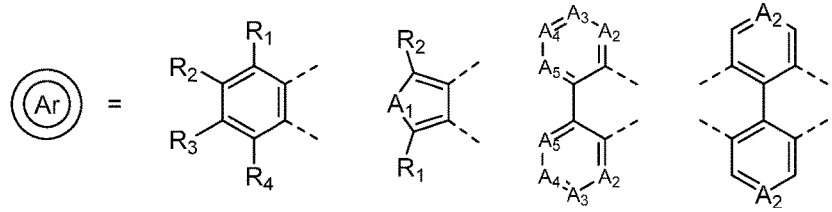
$R_{1, 2, ... 4}$ = $Mt_x$, $CH_3$, $CH_2CH_3$, $CH_2CH_2CH_3$, $CH(CH_3)_2$, $C(CH_3)_3$, $CHCH_2$, $CCH$, $COOMt_x$, $OMt_x$, $OCH_3$, $OCH_2CH_3$, $OCH_2CH_2CH_3$, $CH(CH_3)_2$, $OC(CH_3)_3$, $NH_2$, $NHCH_3$, $N(CH_3)_2$, $NHCH_2CH_2CH_3$, $NHCH(CH_3)_2$, $NHC(CH_3)_3$, $CN$, $Cl$, $Br$, $I$, $SMt_x$, $SO_3Mt_x$
Mt = H, Li, Na, Mg, Ca, Al, or a mixture of these elements
$x$ = 0.33~1
$A_1$ = $NR_1$, O, S
$A_{2, 3, 4, 5}$ = C, N
c
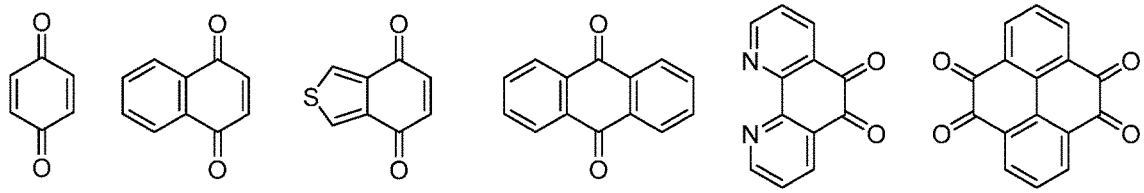
FIGS. 3a-3c

HIGH IONIC CONDUCTIVITY RECHARGEABLE SOLID STATE BATTERIES WITH AN ORGANIC ELECTRODE

RELATED APPLICATIONS

This application claims the benefit of U.S. Provisional Patent Application No. 62/307,079 filed on Mar. 11, 2016, which is incorporated herein by reference.

FIELD OF THE INVENTION

This invention relates to rechargeable solid-state batteries with high ionic conductivity comprising an organic electrode.

BACKGROUND OF INVENTION

Li-ion batteries are in massive commercial adoption and manufacturing that will lower costs and catalyze the growth of energy storage in both vehicle and stationary applications. However, Li-ion technology manufactured today has performance limitations that incremental progress cannot address: (1) the energy density is limited by the amount of charge that can be practically stored via the intercalation mechanism, (2) thermally activated degradation mechanisms limit the upper operating temperature to 50° C. and require cooling systems, and (3) the use of organic carbonate electrolyte results in cells with intrinsic flammability concerns. Such limitations could be potentially overcome by replacing the negative electrode with Li metal, and the liquid electrolytes in the separator and the porous positive electrode with solid ion conductors to form rechargeable solid-state batteries. Rechargeable solid-state batteries open a path to cost competitive cells, while improvements in the thermal stability and safety will have significant benefits at the system level by reducing packaging and controls and creating design flexibility.

In the US today, about 4% of new light-duty vehicles contain a partially or fully electrified powertrain. Further improvements to batteries are widely recognized as a key barrier to wider adoption. A 10% increase in electrified powertrains will reduce US oil consumption by 3%, total US energy use by 1%, and total US $CO_2$ emissions by 1% as well as reduce emissions of $NO_x$ and other combustion products. In addition to impacts on vehicles, cell technology that is energy dense, thermally stable, and non-flammable will be of interest for grid storage, particularly in dense urban environments.

Compared to inorganic materials conventionally used in commercial lithium ion batteries, redox-active organic insertion materials (OIM) are composed of naturally abundant elements (C, H, N, O, S) and their redox-potential and specific capacity could be tailored through molecular structure design, providing almost unlimited choices. OIMs are crystalline organic molecules with well-understood redox-active functional groups that reversibly store/release metal cations via an insertion reaction. Some structurally simple and low-cost OIMs (e.g. benzoquinone and derivatives) have redox potentials of 2.5-3.0 V vs Li and specific capacities of 350-600 mAh/g. These OIMs have been proposed by several research groups as cathode materials for lithium ion batteries, but showed polysulfide-like dissolution-induced capacity decay in traditional liquid electrolyte cells. Such capacity decay can be mitigated by polymerization and functionalization of simple OIMs, but both methods led to complicated synthesis (hence increased cost) and decreased specific capacity (due to increased molecular weight). Some examples of batteries utilizing an organic active material electrode exist, but utilize liquid electrolytes. Further, examples of batteries using an organic electrode active material and a composite polymer electrolyte exist, but the composite polymer demonstrates poor ionic conductivity. Most existing rechargeable solid-state batteries are made using inorganic cathode active materials such as oxides and sulfides, but it is still challenging to simultaneously obtain high energy density and structural reversibility.

It is therefore desirable to provide a completely solid-state battery that uses OIMs and a solid-state electrolyte with high ionic conductivity for better performance. Cycling stability can be improved due to dissolution-free characteristics during the charge and discharge cycling of OIMS because no liquid exists in the cell.

SUMMARY OF INVENTION

In one embodiment, a battery may be rechargeable. Further, all of the components of the battery may comprise solid-state materials or the battery may be an all-solid-state battery. In some embodiments, the battery may be based on a new class of sustainable organic active materials comprising carbonyl groups, which are non-toxic, non-hazardous, completely bio-renewable, and of high capacity (e.g. >400 mAh $g^{-1}$).

In some embodiments, the battery may provide quinone-based cathodes that eliminate current problems arising from high-temperature, corrosive, reactive, and dangerous liquid anolyte and catholyte systems (e.g. Na—S batteries); flammable organic liquid batteries (e.g. Na-ion systems); and low-energy-density and corrosive and dangerous liquid designs (e.g. V-flow systems). In some embodiments, the battery may provide a cathode that comprises a quinone compound when the battery is charged. In some embodiments, the battery may provide an electrolyte that comprises at least one ion-conducting inorganic compound. In some embodiments, the ion-conducting inorganic compound may have a formula of $A_xB_yC_z$, where A is chosen from Li, Na, or combinations thereof, B is chosen from P, As, Si, Ge, Sn, Pb, B, Al, Ga, In, Tl, Ca, Ba, Ti, Cu, Ag, Zn, La, Ce, V, Ta, or combinations thereof, C is chosen from 0, N, S, Se, Sn, or combinations thereof, x/z=0.5-1.0, and y/z=0.2-0.6. In some embodiments, the battery may provide a metallic anode that comprises Li, Na, or an alloy that includes Li or Na. The new battery is based on a benign and scalable solid-stack design that operates reversibly, near room temperature, and/or at high energy densities. Further, all materials to be used can be sourced from renewable and recyclable materials, and the battery design can be optimized for recycling.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 3a-3c shows the structure of quinones that can be used as the cathode active materials for the solid state battery, Including (a) general structure of quinones comprising the 1,2-benzoquinone and 1,4-benzoquinone substructures; (b) Examples for functionalization of quinones; (c) Examples of specific quinones;

DETAILED DESCRIPTION

Figure 1:
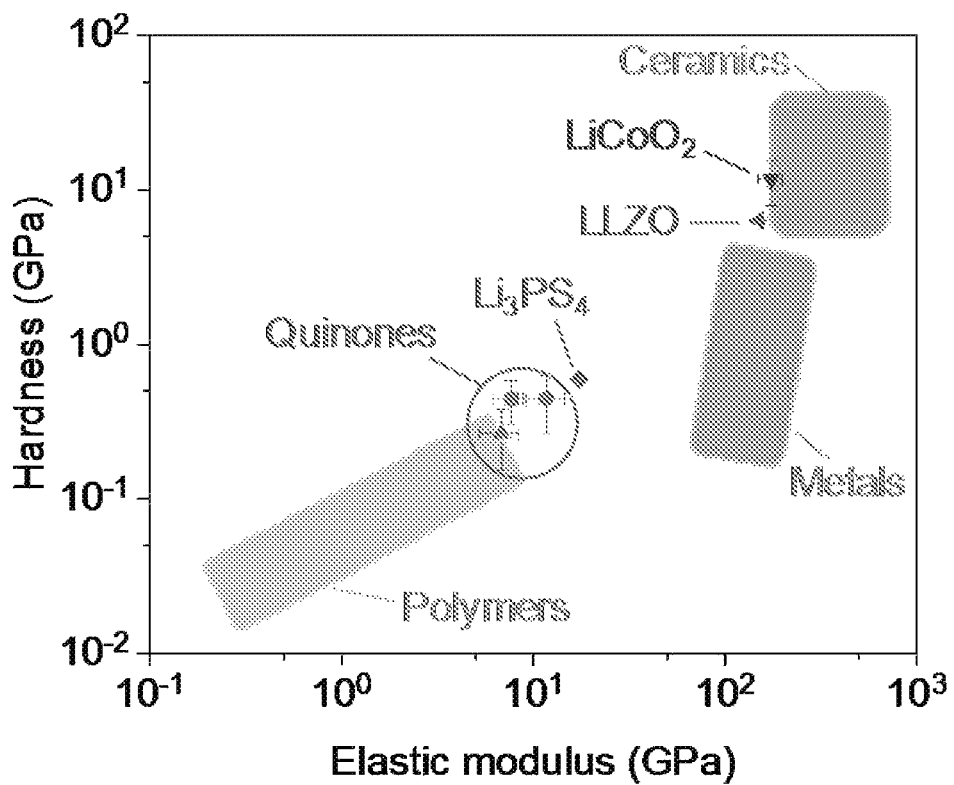
FIG. 1 compares the mechanical properties of quinones and electrolyte/electrode materials used in solid-state batteries.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

"Solid-state" as utilized herein shall be understood to indicate that component(s) of a battery are entirely formed from solid materials. For example, electrodes or electrolytes of a battery may include multiple types of materials, some of which may be aqueous in a conventional battery. However, in a solid-state batteries or solid-state electrolytes, the entirety of the materials making up the battery or electrolytes is entirely solid. In some cases, the solid-state materials may be crystalline, semi-crystalline, or amorphous.

Batteries where quinones are used as cathode active materials most commonly use liquid/quasi-solid organic electrolytes which form intimate contact with quinones and provide efficient ion conduction path. However, nonpolymeric quinones usually exhibit poor cyclability in these electrolytes because of dissolution. The solid-state electrolytes in the current disclosure eliminate such dissolution problem and make it possible for any quinone active materials to operate stably.

In prior work discussed in U.S. Pat. App. Pub. 2014/0308581, Intl Pub. WO 2016/025734, and Int'l Pub. WO 2016/191292, all incorporated by reference herein, various types of batteries utilizing organic electrodes are discussed. The prior works noted above discuss batteries with organic electrode active materials with aqueous electrolytes where low-potential (e.g. <1 V vs Li) metal anodes with materials such as lithium or sodium cannot be used. The solid-state electrolytes in the current disclosure are compatible with such anodes, enabling high-voltage batteries with quinone as the cathode.

U.S. Pat. App. Pub. 2012/0196182, shows a battery comprising a positive electrode made of 1,4-benzoquinone compound with lower alkoxy groups and a solid glass-crystalline electrolyte. However, this battery cannot be characterized as a solid-state cell because 50 μL liquid electrolyte of lithium perchlorate in γ-butyl lactone (1.0 mol $L^{-1}$) was added in the positive electrolyte to impregnate a carbon paper. The solid-state batteries in the current disclosure do not comprise such volatile liquid organic electrolytes, therefore will avoid safety issues due to thermal runaway related to such flammables.

In Zhu et al., *All-Solid-State Lithium Organic Battery with Composite Polymer Electrolyte and Pillar[5]quinone Cathode*, J. Am. Chem. Soc., 2014, 136 (47), pp 16461-16464, an all-solid-state lithium battery based on an organic pillar[5] quinone cathode is discussed. However, the battery uses a composite polymer electrolyte made of poly(methacrylate)-poly(ethylene glycol) and $LiClO_4$ mixed with 3 wt. % $SiO_2$ nanoparticles. Such dry solid polymer electrolytes are easier to process and form intimate contact with electrode active materials compared with inorganic ones, but also exhibit low ionic conductivity in the order of $10^{-6}$-$10^{-4}$ S $cm^{-1}$ at room temperature, which limits battery performance at high current densities. The solid-state electrolytes in the current disclosure have high ionic conductivities of $10^{-5}$-$10^{-2}$ S $cm^{-1}$ at room temperature, therefore will enable much better high-current performance.

Rechargeable solid-state batteries with high ionic conductivity are discussed herein. Notably, such solid-state batteries are made entirely from solid-state materials. In some embodiments, the cathode, electrolyte, and anode of the battery may be formed from solid-state materials. Further, any supports, binders, current collectors, or any other components that may be present in a battery are also formed of solid-state materials. In some embodiments, the solid-state batteries are formed from a cathode formed from at least one organic active material, an ion-conducting inorganic solid-state electrolyte, and a metallic anode.

FIG. 1 compares the mechanical properties of polymer electrolytes, metals, ceramics, quinones, and electrolyte/electrode materials used in solid-state batteries. Quinones have smaller hardness and elastic modulus than those of sulfide-based $Li^+$ conductor $Li_3PS_4$, oxide-based $Li^+$ conductor LLZO, and oxide cathode $LiCoO_2$, which are beneficial for formation of intimate 2D contacts with electrolytes by simple cold-pressing.

Figure 2:
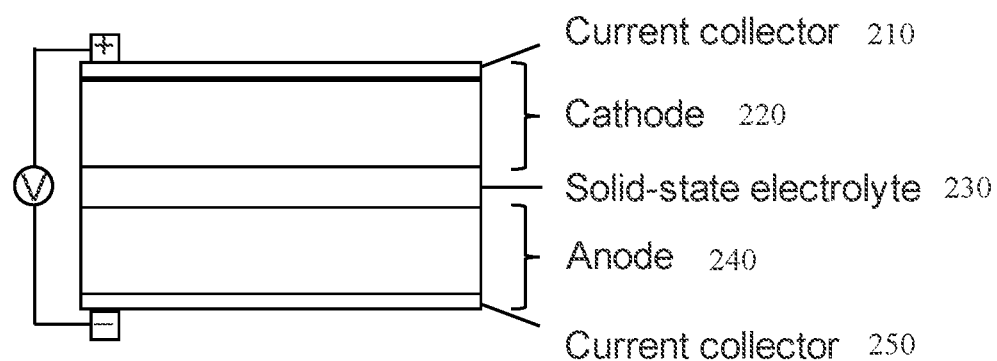
FIG. 2 is nonlimiting example of a schematic of an all-solid state battery.

FIG. 2 is a partial cross-sectional schematic view of a nonlimiting example of a rechargeable solid-state battery discussed herein. The battery may comprise (from top to bottom) a first current collector 210 (optional) to a cathode 220 formed from a cathode mixture. A layer of solid-state electrolyte 230 separates the cathode from an anode layer 240, and a second current collector 250 (optional) may be provided below the anode 240. The cathode 220 is in contact with the electrolyte 230, and anode 240 is also in contact with the electrolyte. However, the cathode 220 and anode 240 are electrically isolated from each other to prevent a short. It should be noted that the term contact as utilized herein refers to electrical contact and does not preclude the use of an intermediate material, such as a conductive adhesive or the like.

The batteries discussed herein are solid-state batteries formed entirely from solid-state materials. It shall be understood by one of ordinary skill in the art that various battery components may include materials to aid bonding, structural rigidity, or the like that do not influence the performance of the battery, which may be characterized as inactive materials. The discussion provided herein regarding electrodes, electrolytes, cathodes, anodes, and the like generally refers to the active materials of such components, or more particularly the materials that are electroactive during charging-discharging, unless stated otherwise. In some embodiments, the battery may provide a cathode where the electrode materials are formed entirely of organic electrode material(s) serving as the active material of the electrode. In some embodiments, the cathode may be formed from at least one organic electrode material. In some embodiments, the battery may provide a cathode formed from the organic electrode active materials or organic carbonyl compounds discussed in U.S. Pat. App. Pub. 2014/0308581, Intl Pub. WO 2016/025734, or Int'l Pub. WO 2016/191292. In some embodiments, the cathode may be formed from at least one quinone. In some embodiments, the quinone comprises molecular compounds chosen from FIG. 3. It should be noted that the quinones are a nonlimiting example of OIMs that are the active material of the electrode as discussed previously above. In some embodiments, the carbonyl groups of the quinone can be in oxidized form or in reduced form (e.g., coordinated to alkali metal ions). In some embodiments, a carbonyl group of the at least one quinone can be reduced into a phenolate and coordinated to an alkali metal ions during discharge or vice versa during charging. In some embodiments, the at least one quinone has an —OM group, where M=Li or Na, directly attached to the quinone core, and that oxidized into carbonyl groups and release $M^+$ ions. Organic quinone materials have high specific capacity enabled by multiple electron transfer reactions, sustainable, environmentally friendly, and potentially low cost. In addition, organic quinone materials can leverage rich organic chemistry to fine-tune functional groups in the chemical structure to optimize the active material-solid electrolyte interfacial interaction for reducing the interface resistance.

Some OIMs have shown decent electronic (~$10^{-4}$ S/cm) and ionic conductivity (~$10^{-6}$ S/cm). Therefore, kinetics-improving strategies used for sulfur electrodes such as a large liquid electrolyte/sulfur ratio which significantly reduces specific energy and preparation of sophisticated nanostructured composite are generally not necessary for OIMs. In addition, the operating potentials of OIMs are ~1 V lower than those of transition metal oxides (for example $LiCoO_2$), which puts lower requirement on the anodic stability of electrolytes. As a result, wider choices in solid electrolytes and more stable cathode-electrolyte interfacial properties can be expected.

The battery may also provide a counter electrode with an organic or inorganic electrode active material. The counter electrode or anode is formed entirely from solid state materials. In some embodiments, the counter electrode is formed from a material that includes at least one alkali metal. The counter electrode is capable of alloying and dealloying; deposition and stripping; and/or storing and releasing of the alkali metal(s). In some embodiments, the alkali metal may be chosen from lithium (Li), sodium (Na), or combinations thereof. As a nonlimiting example, the counter electrode may be an alloy containing Li or Na, such as $Li_xIn$ (x=0-4.33) and $Na_ySn$ (y=0-3.75). In some embodiments, the counter electrode may release alkali metal cations during discharging of the battery into the electrolyte. Further, phenolates may be formed at the anode as well.

The electrolyte comprises an inorganic compound that is ion-conducting. The electrolyte is formed entirely from solid state materials. In some embodiments, the electrolyte is entirely inorganic. The inorganic compound may be in a fully amorphous phase, partially amorphous and crystalline phase, or fully crystalline phase. In some embodiments, the inorganic compound may have a formula of $A_xB_yC_z$, where A is chosen from Li, Na, or combinations thereof, B is chosen from P, As, Si, Ge, Sn, Pb, B, Al, Ga, In, Tl, Ca, Ba, Ti, Cu, Ag, Zn, La, Ce, V, Ta, or combinations thereof, C is chosen from O, N, S, Se, Sn, or combinations thereof, x/z=0.5–1.0, and y/z=0.2–0.6. In some embodiments, the solid state electrolyte may be selected from sulfides (glass, glass-ceramic, and ceramic), oxides (LISICON, NASICON, garnet, etc.), and Li phosphorus oxynitride (LiPON). In some embodiments, the solid state electrolyte may be selected from $Li_2S$—$P_2S_5$, $Li_2S$—$SiS_2$, $Li_2S$—$P_2S_5$—$GeS_2$, $Li_3PS_4$, $Li_7P_3S_{11}$, $Li_4P_2S_6$, $Li_{10}GeP_2S_{12}$, garnet-type $Li_7La_3Zr_{2-x}Nb_xO_{12}$ (M=Nb, Ta, Al, 0≤x≤0.5), perovskite-type $La_{0.5}Li_{0.5}TiO_3$, LiPON, $Na_3PS_4$, $Na_3SbS_4$, $Na_2S$—$P_2S_5$, $Na_{10}GeP_2S_{12}$, $Na_3PSe_4$, $Na_{3+x}M_xP_{1-x}S_4$ (M=Si, Ge, and Sn, 0≤x≤1), or $Na_3Zr_2Si_2PO_{12}$. In some embodiments, the solid state electrolyte may be selected from, but not limited to, $Na_{3+x}P_{1-x}Si_xSe_4$ (0≤x≤1), $Na_3PSe_{4-x}O_x$ (0≤x≤4).

In some embodiments, the ionic conductivity of the solid-state electrolyte is higher than $10^{-5}$ S $cm^1$ at room temperature.

In some embodiments, a support may be optionally provided for electrode(s) of the battery. The electrode materials may be positioned on the support, for example quinone may be positioned on the support. In some embodiments, an electrode may be formed on the support by a slurry or ink coating process in a roll-to-roll fashion. In some embodiments, a solid-state electrolyte may also be positioned on the support. In some embodiments, an electrolyte may be cold-pressed to the electrode. Further, an optional polymer binder may also be provided to bind materials to support. As a nonlimiting example, the polymer binder may be selected from polytetrafluoroethylene, polyvinylidene fluoride, polyethylene oxide, poly(3,4-ethylenedioxythiophene) polystyrene sulfonate, polyacrylates, carboxymethylcellulose and its Li or Na salts, and alginate and its Li or Na salts. In some embodiments, the support may have a structure selected from foam, foil, or mesh. In some embodiments, the support may be constructed of at least one element selected from a Group 4, 8, 10, 11, 13, or 14 elements.

In some embodiments, the organic electrode active material or cathode active material may be an organic carbonyl compound (OCC). In some embodiments, the electrode may be a quinone. In some embodiments, the quinone may comprise molecular compounds chosen from FIGS. 3a-3c. In some embodiments, the carbonyl groups of the quinone are reduced and coordinated to alkali metal ions. Further, the organic electrode active material may be mixed with at least one solid electrolyte. In some embodiments, at least one conductive agent may also be provided. The solid electrolyte may include inorganic compound, and may be in a fully amorphous phase, partially amorphous and crystalline phase, or fully crystalline phase. The inorganic compound may have a formula of $A_xB_yC_z$, where A is chosen from Li, Na, or combinations thereof, B is chosen from P, As, Si, Ge, Sn, Pb, B, Al, Ga, In, Tl, Ca, Ba, Ti, Cu, Ag, Zn, La, Ce, V, Ta, or combinations thereof, C is chosen from O, N, S, Se, Sn or combinations thereof, $x/z=0.5-1.0$, and $y/z=0.2-0.6$. Further, in some embodiments, the counter electrode is formed from a material that includes at least one alkali metal. In some embodiments, the alkali metal may be chosen from lithium (Li), sodium (Na), or combinations thereof.

Figures 4A, 4B:
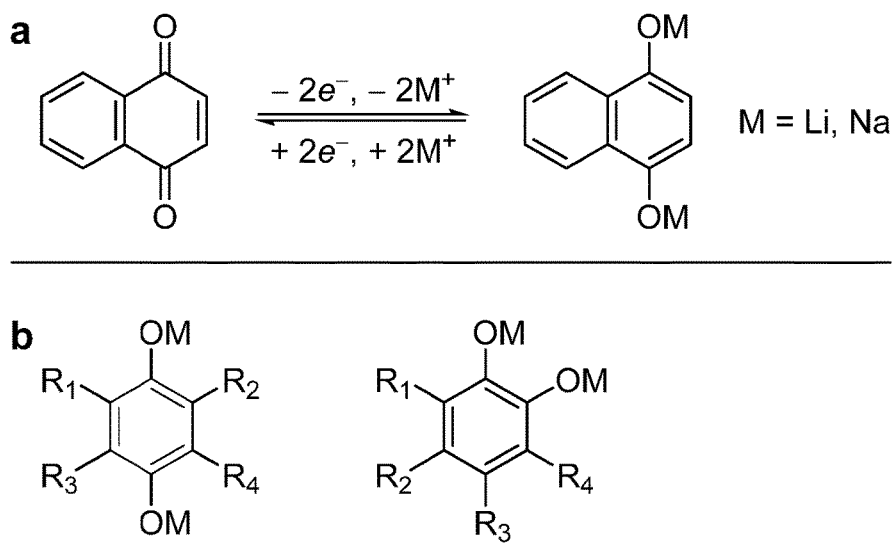
FIGS. 4a-4b shows (a) the mechanism of the reversible electrochemical reduction of a quinone and (b) the general structure of quinones at their reduced form.

FIGS. 3a-3c show the structure of the oxidized form of quinones, included in the general term of quinones, that can be used as electrode active materials for the solid state battery. FIG. 4a-4b show a nonlimiting example of the structure of the reduced form of quinones that can be used as the electrode active materials for the solid state battery. Generally, the various organic materials discussed in U.S. Pat. App. Pub. 2014/0308581, Intl Pub. WO 2016/025734, and Intl Pub. WO 2016/191292 including organic carbonyl compounds (OCCs) may be reduced and coordinated to alkali metal ions. Similarly, the quinones shown in FIGS. 3a-3c may be are reduced and coordinated to alkali metal ions. As nonlimiting examples, alkali metal salts of 1,4-dihydroxynaphthalene (FIG. 4a) and $Li_4Na_2C_6O_6$ (FIG. 5) are both reduced forms of quinones. When reversibly oxidized to their carbonyl-containing state, they become quinones 1,4-naphthoquinone and $Li_2Na_2C_6O_6$, respectively. The reduced form of organic carbonyl polymers may also serve as electrode active materials like those shown in FIGS. 3a-3c.

In some embodiments, the battery may form a reduced quinone cathode having phenolate structures as the battery discharges from a charged state. Further, alkali metal cations, e.g. Li or Na, may be released from the anode into the electrolyte, forming phenolates at the anode. As the battery charges from a discharged state, alkali metal cations, e.g. Li and Na, may be alloyed/deposited/stored at the anode. Further, alkali metal cations may be released from the cathode into the electrolyte, forming quinone at the cathode. In some embodiments, the quinone is reduced by (1) electrochemical reduction in a Li- or Na-containing electrolyte and (2) chemical reduction with a Li or Na salt.

For the various molecular structures shown in FIGS. 3a-4b, the $R_1, R_2 \ldots R_4$ options shown may be applicable the various structures shown in these figures provide an $R_N$ group. Further, it shall be understood that items listing multiple options do not preclude repetition of a particular option within a molecular structure. For example, selecting $R_1=Mt_x$ does not preclude $Mt_x$ being selected for $R_{2, 3, and/or 4}$. Nonlimiting examples of the electrode active material may include $Li_2Na_2C_6O_6$, which has never been reported in a solid-state battery. The first prototype of such a device made of $Li_2Na_2C_6O_6$ was demonstrated in Example 1. Other nonlimiting examples of electrode active materials may include $Na_2C_6O_6$, 1,4-benzoquinone, 1,4-naphthoquinone, benzo[c]thiophene-4,7-dione, anthracene-9,10-dione, 1,10-phenanthroline-5,6-dione, pyrene-4,5,9,10-tetraone, or combinations thereof (FIG. 3c).

Figure 5:
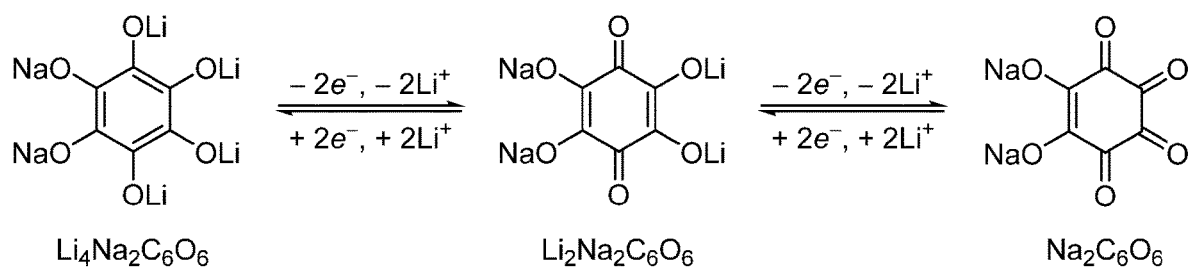
FIG. 5 shows an example where —OM groups (M=Li and Na) directly attached to a quinone core can be oxidized into carbonyl groups and release $M^+$ ions.

The electroactivity of compounds shown in FIGS. 3a-4b originates from the reversible electrochemical reduction reaction of carbonyl groups and the ability of the negatively charged oxygen atoms to coordinate to metal ions (e.g. FIG. 4b and FIG. 5). This "cation coordination" is intrinsically fast and highly reversible.

In some embodiments, the molecular engineering of quinones focuses on two materials, p-benzoquinone and o-benzoquinone, which undergo reversible two-electron redox reactions. Derivation of these materials results in two classes of quinones with high specific capacities of 477 mAh $g^{-1}$. The functionalization of these materials with aromatic rings improves the electronic interaction between molecules, which increases the electronic conductivity of the materials. Introduction of heteroatoms to the molecules facilitates ion transport, and incorporation of multiple molecules in a single molecular unit results in quinones with both high capacity and vacant sites for further structural modification. Density functional theory (DFT) calculations can be used to assess energy levels of the lowest unoccupied molecular orbital and the free energy change of the quinones upon lithiation/sodiation. The results can give good estimates of the charge/discharge potential of the quinones.

It should be understood that quinones may be converted to phenolates upon reduction (e.g. FIG. 4b) and carbonyl compounds upon oxidation (e.g. FIG. 5). These types of conversions are reversible and may repeat during the charge-discharge cycling of a solid-state battery.

In contrast to traditional solid-state electrodes fabricated using dry process without solvents, in some embodiments, a quinone cathode can be manufactured by slurry or ink coating process in a roll-to-roll fashion. Compounds presented in FIGS. 3a-4b and U.S. Pat. App. Pub. 2014/0308581, Int'l Pub. WO 2016/025734, and Int'l Pub. WO 2016/191292 are soluble in solvents, such as, but not limited to, dimethylformamide, n-methyl-2-pyrrolidone, water, ethanol, acetone, acetonitrile, gamma lactone, ethyl acetate, glycol dimethyl ether, chlorobenzene, 1,2-chlorobenzene, chloroform, dichloromethane, etc. As a nonlimiting example, 1,4-benzoquinone is soluble in acetone. In some embodiments, the fully dissolved quinones can be finely mixed with solid state electrolyte powder to form a slurry. In some embodiments, the fully dissolved quinones can be finely mixed with soluble solid-state electrolyte precursor to form an ink. In cases where the quinones are insoluble in any solvent, then the quinone may be provided as a powder, and can be finely mixed with a soluble solid-state electrolyte precursor to form a slurry. It is understood in the field that organic binders may be added to form a stable slurry or ink with desirable properties, such as desired viscosity, adhesion, surface tension, or the like for roll-to-roll processing. Such slurry or ink can then be coated in a roll-to-roll fashion either by doctor-blade method or ultrasonically spray method on substrates. After the solvent is removed during drying, the electrodes may be compressed to reduce porosity and increase interface conductivity.

Experimental Example 1 ($Li_2Na_2C_6O_6$) in Li-Ion Cell

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Figure 6:
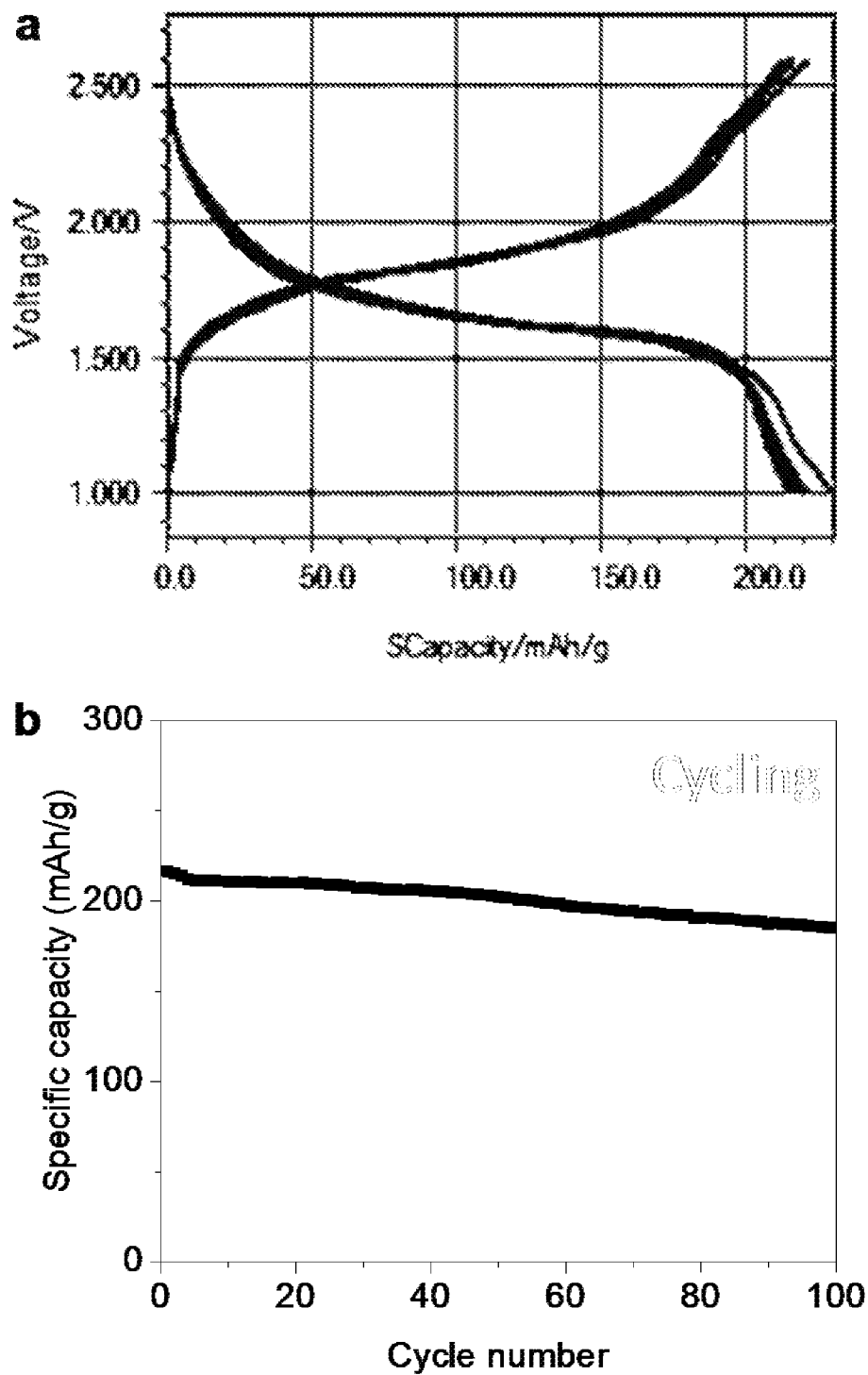
FIGS. 6a-6b show the (a) voltage profile and (b) cycling performance of $Li_2Na_2C_6O_6$ measured with a solid-state $Li^+$-conducting electrolyte.

All-solid state prototype cells based on Li and/or Na metals and quinones have been built and demonstrated excellent electrochemical performance in laboratory testing. We freeze-milled $Na_2C_6O_6$ and mixed with carbon nanotube at 9:1 weight ratio. FIG. 6a shows the voltage profile of such a battery measured with a solid state $Li^+$-conducting electrolyte and a Li metal as an anode. The electrolyte used in this example is amorphous $75Li_2S\text{-}25P_2S_5$ (mol. %). FIG. 6*b* shows the cycling performance of a quinone measured with a solid-state $Li^+$-conducting electrolyte.

Experimental Example 2 ($Na_2C_6O_6$) in Na-Ion Cell

Figure 7:
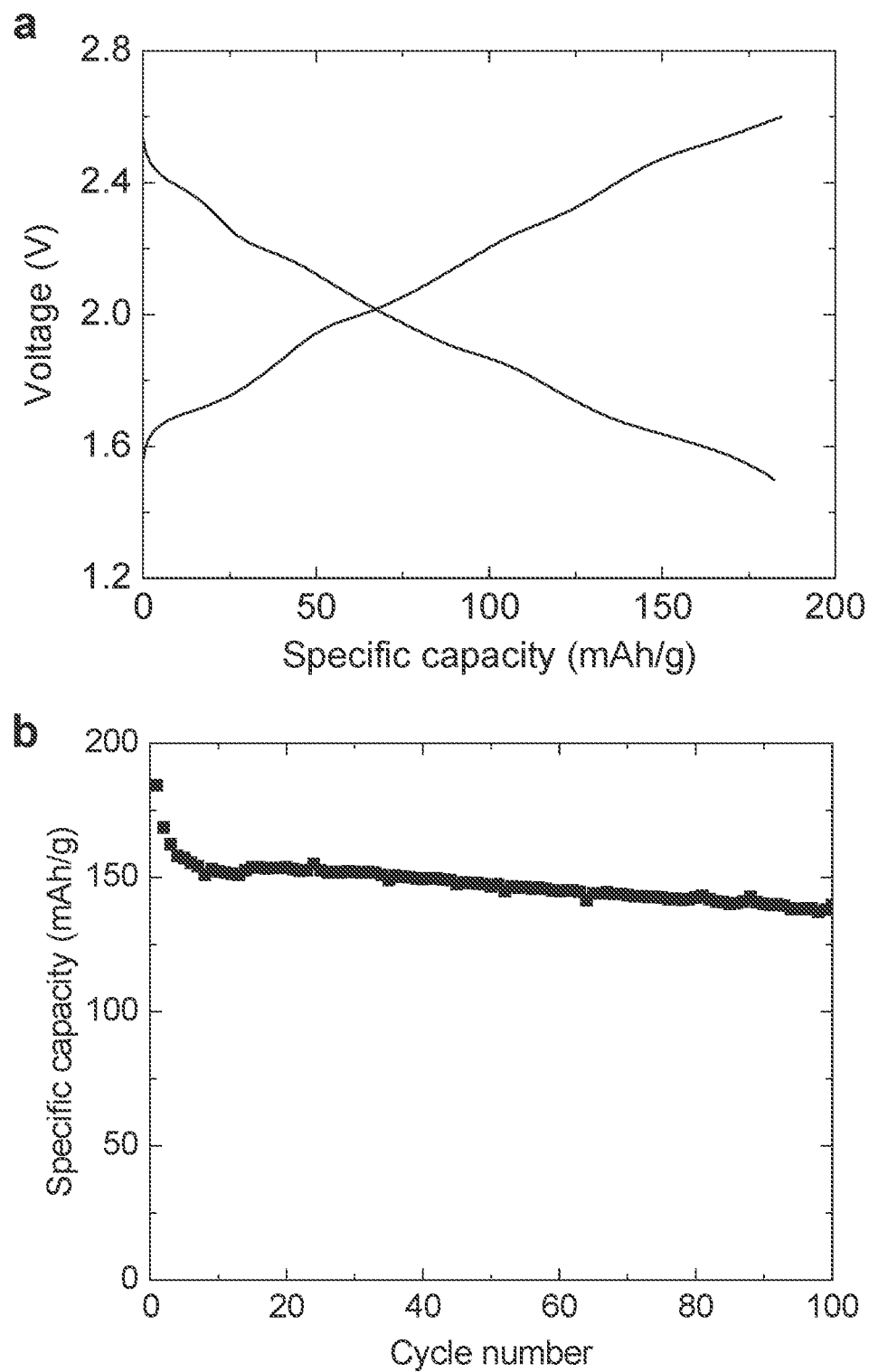
FIGS. 7a-7b show the (a) voltage profile and (b) cycling performance of $Na_2C_6O_6C$ measured with a solid-state $Na^+$-conducting electrolyte.

Quinones have also been evaluated for solid-state sodium batteries. FIGS. 7*a*-7*b* respectively show the voltage profile and cycling performance of such a battery measured with a solid-state $Na^+$-conducting electrolyte and a $Na_{15}Sn_4$ anode. The electrolyte used in this example is glass-ceramic $Na_3PS_4$.

Based on the ability of carbonyl oxygen atoms to coordinate various alkali ions ($Li^+$, $Na^+$, $K^+$, $Mg^{2+}$, etc.), quinone-based all-solid state cells using K and Mg can also be expected to work.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A battery formed of solid-state materials, the battery comprising:
    a cathode comprising active materials that, are organic and comprise at least one quinone substructure, wherein the redox-active groups in the active materials consist of the at least one quinone substructure, where carbonyl groups (C=O) are reduced into C—OM groups (M=Li or Na) during discharge, and the C—OM groups oxidized into carbonyl groups during charge;
    an electrolyte in contact with the cathode, wherein the electrolyte is entirely inorganic, wherein the electrolyte comprises at least one inorganic compound that is ion-conducting, wherein the at least one inorganic compound has a formula of $A_xB_yC_z$,
    where A is chosen from Li, Na or combinations thereof,
    B is chosen from P, As, Si, Ge, Sn, Pb, B, Al, Ga, In, Tl, Ca, Ba, Ti, Cu, Ag, Zn, La, Ce, V, Ta, or combinations thereof,
    C is chosen from O, N, S, Se, Sn, or combinations thereof,
    $x/z$=0.5-1.0 and
    $y/z$=0.2-0.6; and
    an anode comprising an alkali metal, wherein the anode is in contact with the electrolyte and electrically isolated from the cathode, and all materials making up the cathode, the electrolyte, and the anode are solid-state materials.

2. The battery of claim 1, wherein the electrolyte is crystalline, semi-crystalline, or amorphous.

3. The battery of claim 1, wherein the at least one quinone comprises 1,2-benzoquinone and 1,4-benzoquinone substructures.

4. The battery of claim 1, wherein a carbonyl group of the at least one quinone is reduced into a phenolate and coordinated to an alkali metal ion during discharge.

5. The battery of claim 1, wherein the anode comprises Li, Na, or an alloy comprising Li or Na.

6. The battery of claim 5, wherein the anode is capable of (de)alloying/deposition-stripping/storing-releasing of at least one metal-ion chosen from Li, Na, or combinations thereof during charge-discharge of the battery.

7. The battery of claim 1, wherein the electrolyte has high ionic conductivity of $10^{-3}$ to $10^{-2}$ S cm$^{-1}$ at room temperature.

\* \* \* \* \*